US010966599B2

(12) United States Patent
Park et al.

(10) Patent No.: US 10,966,599 B2
(45) Date of Patent: Apr. 6, 2021

(54) ENDOSCOPIC STEREO MATCHING METHOD AND APPARATUS USING DIRECT ATTENUATION MODEL

(71) Applicant: Korea Electronics Technology Institute, Seongnam-si (KR)

(72) Inventors: Min Gyu Park, Seongnam-si (KR); Young Bae Hwang, Seoul (KR); Ju Hong Yoon, Sejong-si (KR)

(73) Assignee: Korea Electronics Technology Institute, Seongnam-si (KR)

( * ) Notice: Subject to any disclaimer, the term of this patent is extended or adjusted under 35 U.S.C. 154(b) by 76 days.

(21) Appl. No.: 16/424,546

(22) Filed: May 29, 2019

(65) Prior Publication Data

US 2019/0365213 A1 Dec. 5, 2019

(30) Foreign Application Priority Data

May 31, 2018 (KR) .................. 10-2018-0062438

(51) Int. Cl.
*A61B 1/05* (2006.01)
*A61B 1/06* (2006.01)
*H04N 5/225* (2006.01)
*H04N 13/239* (2018.01)
*H04N 13/00* (2018.01)

(52) U.S. Cl.
CPC .............. *A61B 1/05* (2013.01); *A61B 1/0676* (2013.01); *A61B 1/0684* (2013.01); *H04N 5/2256* (2013.01); *H04N 13/239* (2018.05); *H04N 2005/2255* (2013.01); *H04N 2013/0081* (2013.01)

(58) Field of Classification Search
CPC ....... A61B 1/05; A61B 1/0684; A61B 1/0676; H04N 13/239; H04N 5/2256; H04N 2013/0081
See application file for complete search history.

(56) References Cited

U.S. PATENT DOCUMENTS 8,968,332 B2 * 3/2015 Farritor ................ A61B 5/062
606/130

FOREIGN PATENT DOCUMENTS

KR 10-2010-0051477 A 5/2010
KR 10-2012-0117165 A 10/2012

OTHER PUBLICATIONS

Zhu et al: "A Fast Single Image Haze Removal Algorithm Using Color Attenuation Prior", IEEE, 2015 (Year: 2015).*
Hirschmuller, "Stereo Processing by Semiglobal Matching and Mutual Information", IEEE, 2008.*
He et al, "Single Image Haze Removal Using Dark Channel Prior", IEEE, 2011 (Year: 2011).*

(Continued)

*Primary Examiner* — Ruiping Li
(74) *Attorney, Agent, or Firm* — NSIP Law

(57) ABSTRACT

An endoscopic stereo matching method and apparatus using a direct attenuation model is provided. A method for generating a depth image according to an embodiment includes: generating a stereo image; and estimating a depth image from the stereo image based on an attenuation trend of light of an illumination used to generate the stereo image. Accordingly, a dense depth image can be obtained by using images obtained from a capsule endoscope, and thus the geometric structure of the inside of the GI tract can be estimated.

19 Claims, 10 Drawing Sheets

Input

SGM

Proposed

(56) References Cited

OTHER PUBLICATIONS

Korean Office Action dated Jan. 29, 2020 in corresponding Korean Patent Application No. 10-2018-0062438 (2 pages in English, 4 pages in Korean).
Korean Office Action dated Jul. 22, 2019 in corresponding Korean Patent Application No. 10-2018-0062438 (2 pages in English, 4 pages in Korean).
Park et al., "Depth Estimation using Endoscopic Stereo Image," Institute of Control, Robotics and Systems (ICROS), May 17-19, 2018, Republic of Korea (3 pages in Korean with an English Abstract).

* cited by examiner

Input　　　　　　SGM　　　　　　Proposed

Rendered 3D structures of SGM from two different viewpoints

Rendered 3D structures of Proposal from two different viewpoints

Input and disparity map (stomach)

Input and disparity map (small bowel)

Size estimation result 3D structure with and without color textures

Size estimation result 3D structure with and without color textures

ENDOSCOPIC STEREO MATCHING METHOD AND APPARATUS USING DIRECT ATTENUATION MODEL

CROSS-REFERENCE TO RELATED APPLICATION(S) AND CLAIM OF PRIORITY

This application is based on and claims priority under 35 U.S.C. § 119 to Korean Patent Application No. 10-2018-0062438, filed on May 31, 2018, in the Korean Intellectual Property Office, the disclosure of which is herein incorporated by reference in its entirety.

BACKGROUND

Field

The present disclosure relates generally to image processing technology, and more particularly, to a method for estimating depth by using binocular images obtained from the digestive system (the duodenum, stomach, small bowel, large bowel. etc.) through a capsule endoscope.

Description of Related Art

The wireless capsule endoscope (WCE) is a useful device to collect images of the gastrointestinal (GI) tract for screening, diagnostic and therapeutic endoscopic procedures. The WCE may capture the images of the small bowel where a wired endoscopic device cannot reach.

To recognize depth from endoscopic images, various computer vision techniques such as stereo matching, shape-from-shading (SfS), shape-from-focus (SfS), shape-from-motion (SfM), or the like are utilized. They generate 3D meshes through Delaunay triangulation by using triangulated feature points.

Among these techniques, stereo matching is a technique to estimate a depth image from images, and may be divided into an active approach and a passive approach. The stereo matching using structured light may be applied to the active approach which projects a visible or infrared ray (IR) pattern to a scene to be utilized for correspondence searching between images.

However, commercially available WCE products are not capable of estimating depth information and thus the geometric structure of the GI tract captured by a WCE may not be estimated. Accordingly, sizes or shapes of disease symptoms in capsule endoscopic images are diagnosed depending only on experiences of doctors.

SUMMARY

To address the above-discussed deficiencies of the prior art, it is a primary object of the present disclosure to provide a method and an apparatus for estimating depth information regarding an image obtained by a capsule endoscope, as a method for exactly knowing a shape and a size of a disease symptom through real measurement.

A method for generating a depth image according to an embodiment of the present disclosure to achieve the above-described object includes: generating a stereo image; and estimating a depth image from the stereo image based on an attenuation trend of light of an illumination used to generate the stereo image.

In addition, the generating may include generating the stereo image in an environment where there is no external light.

In addition, the estimating the depth image may include estimating the depth image by using the following equation:

$$d(p) = \frac{ln(J(p)) - ln(I(p))}{\beta(p)}$$

where $d(p)$ is a depth of a pixel p, $J(p)$ is a scene radiance of the pixel p, $I(p)$ is an observed intensity of the pixel p, and $\beta(p)$ is a light attenuation coefficient.

In addition, the $\beta(p)$ is a sum of an absorption coefficient and a scattering coefficient of light.

In addition, the generating may include generating an internal stereo image filled with a homogeneous matter.

In addition, the $\beta(p)$ may be approximated as a constant value.

In addition, the $J(p)$ may be approximated as a mean of all pixel values.

In addition, the estimating the depth image may include estimating the depth image by using the following equation:

$$d_\beta(p) = \beta d(p) = ln(\bar{I}) - ln(I(p))$$

where $d_\beta(p)$ is a depth image up to a scale factor $\beta$ regarding the pixel p, $\bar{I}$ is a mean of all pixel values, and $I(p)$ is an observed intensity of the pixel p.

In addition, the scale factor $\beta$ may be determined according to the following equations:

$$\beta = d_\beta(p) / d_s(p)$$
$$d_s(p) = \frac{fB}{|p_x^L - p_x^R|}$$

where $p_x^L$ and $p_x^R$ are positions of matched points from left and right images along an x-axis, f is a focal distance of a left camera, and B is a distance between cameras.

An image system according to another embodiment includes: a stereo camera configured to generate a stereo image; and a computing system configured to estimate a depth image based on an attenuation trend of light of an illumination used to generate the stereo image.

A method for generating a depth image according to another embodiment includes: estimating a depth image from a stereo image based on an attenuation trend of light of an illumination used to generate the stereo image; and outputting the estimated depth image.

An image system according to another embodiment includes: a receiver configured to receive a stereo image; and a computing system configured to estimate a depth image based on an attenuation trend of light of an illumination used to generate the received stereo image.

According to embodiments of the present disclosure as described above, a dense depth image can be obtained by using images obtained from a capsule endoscope, and thus the geometric structure of the inside of the GI tract can be estimated. Accordingly, the shape and size of a disease symptom in the GI tract can be exactly identified through real measurement, such that exact diagnosis and treatment can be achieved.

Other aspects, advantages, and salient features of the invention will become apparent to those skilled in the art from the following detailed description, which, taken in conjunction with the annexed drawings, discloses exemplary embodiments of the invention.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Hereinafter, the present disclosure will be described in detail with reference to the accompanying drawings.

Embodiments of the present disclosure suggest a method for estimating depth by using binocular images obtained from the digestive system ((the duodenum, stomach, small bowel, large bowel, etc.) through stereo camera-based wireless capsule endoscopy.

Specifically, embodiments of the present disclosure grasp the structure of the digestive system by using the attenuation trend of light of an illumination mounted in an endoscope by considering that there is no other external light source except the illumination mounted in the endoscope, and estimate an exact depth image by using corresponding information in stereo matching.

In addition, embodiments of the present disclosure estimate a scale factor by using sparse feature correspondences (SFC), and guide stereo matching to recover the detailed structure of a captured image by using the estimated depth image.

1. Wireless Endoscopic Capsule Device

Figure 1A:
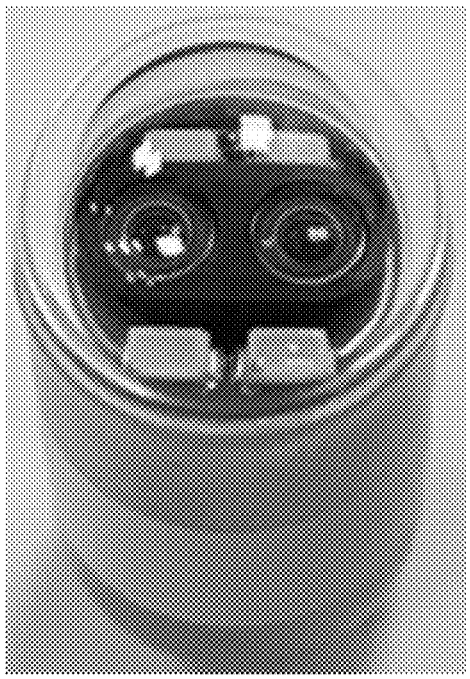
FIGS. 1A and 1B are views illustrating photos of a wireless endoscopic capsule device to which embodiments of the present disclosure are applicable.
Figure 1B:

FIGS. 1A and 1B are views showing photos of a wireless endoscopic capsule device to which embodiments of the present disclosure are applicable. FIG. 1A illustrates a stereo-type wireless endoscopic capsule, and FIG. 1B illustrates a wireless receiver.

As shown in FIGS. 1A and 1B, the wireless endoscopic capsule includes two cameras, four light emitting diode (LED) lights, a wireless transmitter, and a battery. The four LED lights are attached around the cameras and the LED lights are synchronized with the cameras to minimize the battery usage.

Figure 2:
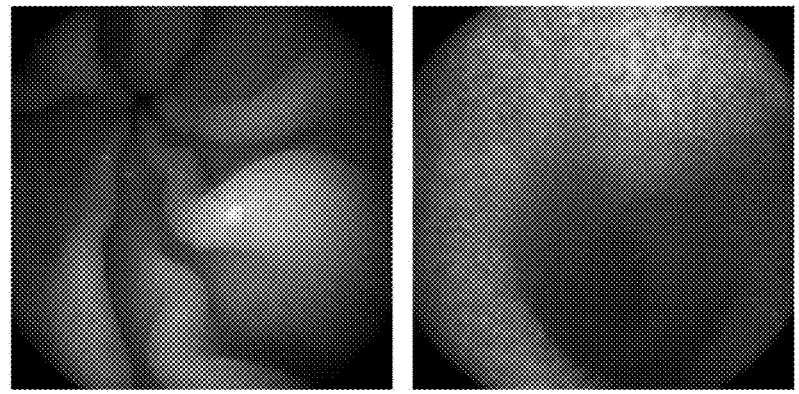
FIG. 2 is a view illustrating images of the inside of the digestive system captured by the wireless endoscopic capsule device suggested in FIGS. 1A and 1B.

The wireless endoscopic capsule device generates images of the inside of the digestive system as shown in FIG. 2 while moving through the GI tract from the stomach to the large bowel. Captured images are transmitted to the wireless receiver because the wireless endoscopic capsule does not have an internal storage device.

2. Depth Estimation Using a Direct Attenuation Model

Since there is no external light source except the lights attached to the wireless endoscopic capsule in the GI tract, farther objects look darker than nearer objects in the generated image. Therefore, the attenuation trend of light is considered to estimate a depth image assuming that the medium in the GI tract is homogenous.

Accordingly, in embodiments of the present disclosure, a computing system generates a stereo image and then estimate a fully dense depth image of a high scale by using a direct attenuation model. Then, the computing system solves the scale ambiguity by using SFC, and utilizes the rescaled depth image to guide semi-global matching (SGM).

Hereinafter, a method for estimating depth by using the direct attenuation model will be described in detail.

Since the generated image has poor visibility, the image for each pixel p may be modeled as shown in Equation 1 presented below:

$$I(p)=J(p)t(p)+A(1-t(p)) \qquad \text{Equation 1}$$

where J is the scene radiance, I is the observed intensity, t is the transmission map, and A is the atmospheric light. Since there is no natural illumination such as sunlight, A may be dropped from Equation 1.

Then, t may be defined as shown in Equation 2 presented below:

$$t(p)=I(p)/J(p) \qquad \text{Equation 2}$$

In addition, the transmission may be defined by Equation 3:

$$t(p)=\exp(-\beta(p)d(p)) \qquad \text{Equation 3}$$

where an attenuation coefficient $\beta(p)$ may be represented by sum of absorption and scattering coefficients, $\beta(p)=\beta_{absorption}(p)+\beta_{scatter}(p)$.

By combining Equations 2 and 3, the depth of the pixel p may be estimated as shown in Equation 4 presented below:

$$d(p) = \frac{\ln(J(p)) - \ln(I(p))}{\beta(p)} \approx \frac{\ln(\bar{I}) - \ln(I(p))}{\beta} \qquad \text{Equation 4}$$

To simplify Equation 4, J(p) and $\beta(p)$ may be approximated by considering characteristics of the GI tract. First, assuming that the GI tract is filled with a homogeneous matter such as water, the attenuation coefficient $\beta(p)$ may be approximated as a constant value for all pixels ($\beta=\beta(p)$).

Second, the scene radiance is approximated as a mean of all pixel values based on the assumption that most pixels have similar colors in a local region of the GI tract ($J(p)\approx\bar{I}$).

Figure 3:
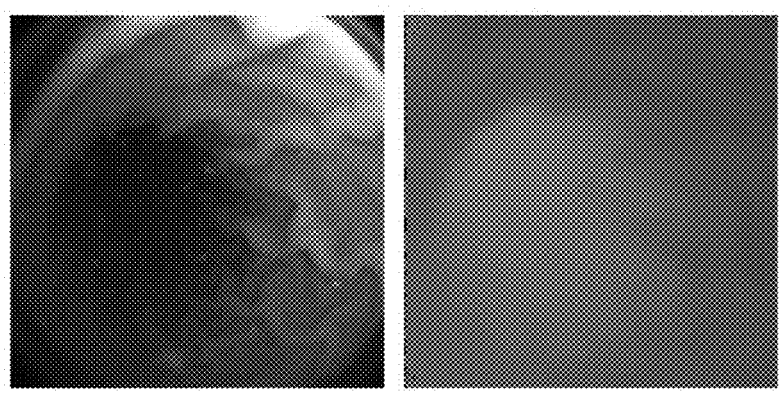
FIGS. 3 and 4 are views illustrating depth images estimated according to an embodiment of the present disclosure.
Figure 4:
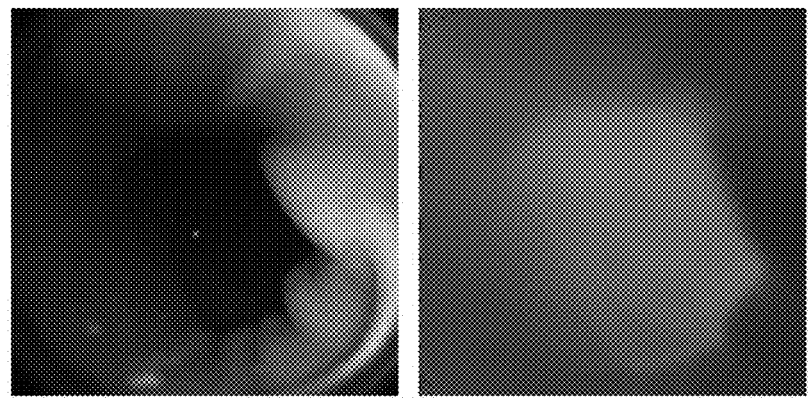

Based on the second assumption, the depth image up to a scale factor β can be easily obtained:

$$d_\beta(p) = \beta d(p) = In(\bar{I}) - In(I(p))$$  Equation 5 where the depth image $d_\beta(p)$ indicates a depth image to the scale factor. FIGS. 3 and 4 illustrate input images and depth images calculated according to Equation 5. Herein, bright pixels indicate that they are farther than dark pixels.

3. Resolving the Scale Ambiguity of $d_\beta$

To resolve the scale ambiguity of $d_\beta(p)$, β is computed by using SPC. To achieve this, corner points are detected and matched. Then, the depth of p $d_s(p)$, is computed according to Equation 6 presented below:

$$d_s(p) = \frac{fB}{|p_x^L - p_x^R|},$$  Equation 6 where $p_x^L$ and $p_x^R$ are the positions of matched points from the left and right images along the x-axis, f is the focal distance of the left camera, and B is the baseline distance between the two cameras. Since each corner point has corresponding $d_\beta(p)$, β may be computed by the following Equation:

$$\beta = d_\beta(p)/d_s(p)$$  Equation 7

Assuming that β is constant for all pixels, optimal β and β* that maximize the number of inlier points whose difference is smaller than a threshold value $\tau_c$ are found.

$$\beta^* = \underset{\beta \in B}{\mathrm{argmax}} \sum_{p \in S} T(p, \beta, \tau_c),$$  Equation 8

$$T(p, \beta, \tau_c) = \begin{cases} 1 & \text{if } |d_s(p) - d_\beta(p)/\beta| \leq \tau_c \\ 0 & \text{otherwise} \end{cases},$$

where B is the set of β values computed from all feature correspondences and S is the set of correspondences' positions in the image coordinate. The function T gives 1 if the discrepancy between $d_s(p)$ and rescaled $d\beta(p)$ is small, and gives 0 otherwise. Therefore, the estimated β* minimizes the gap between $d_s$ and $d_\beta/\beta$. Accordingly, $d_\beta(p)$ is rescaled and a disparity map corresponding thereto is computed according to the following equation:

$$\bar{d}_\beta(p) = \frac{d_\beta(p)}{\beta^*}, \bar{D}_\beta(p) = \frac{fB}{\bar{d}_\beta(p)}$$  Equation 9

The rescaled disparity map $\bar{D}_\beta(p)$ is used to leverage stereo matching.

4. Robust Stereo Matching Using a Guidance Depth Image

To compute the disparity map D(p) to minimize the following energy function, the SGM algorithm is modified as follows:

$$E(d) = \sum_p (\phi(p, D(p)) + \psi(p, D(P))) + \\ \sum_{q \in N_p} P_1 T[|D(p) - D(q)| = 1] + \\ \sum_{q \in N_p} P_2 T[|D(p) - D(q)| > 1]$$  Equation 10

In the first term, the function ϕ(•,•) is the pixel-wise matching cost, computed by using Census-based hamming distance and absolute difference (AD-CENSUS). In addition, the function ψ(•,•) is also the pixel-wise matching cost computed by using $\bar{D}_\beta(p)$.

$$\psi(p, D(p)) = \begin{cases} |\bar{D}_\beta(p) - D(p)| & \text{if } |\bar{D}_\beta(p) - D(p)| \leq \tau_{err} \\ c & \text{otherwise} \end{cases}$$  Equation 11

The second term gives the penalty $P_1$ for pixels having small disparity differences from neighboring pixels (q∈$N_p$). That is, T[|D(p)−D(q)|=1] gives 1 when the difference between the disparity values is 1. Similarly, the third term gives the large penalty $P_2(P_2 > P_1)$ for pixels having disparity difference greater than 1 with neighboring pixels. Equation 10 is minimized by using the SGM method.

As post-processing, the weighted median filter is applied. Finally, a depth image is obtained from the disparity map by d(p)=fB/D(p).

5. Experimental Results

Figure 5A:
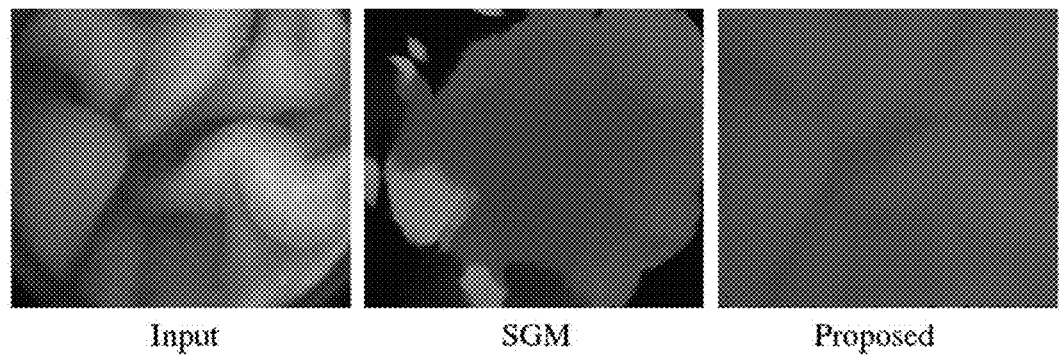
FIGS. 5A to 5C, 6A to 6D, and 7A to 7D are views illustrating images indicating results of endoscopic stereo matching according to an embodiment of the present disclosure.
Figure 5B:
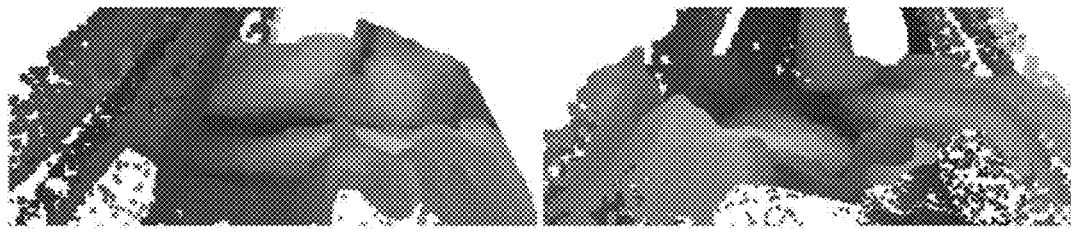
Figure 5C:
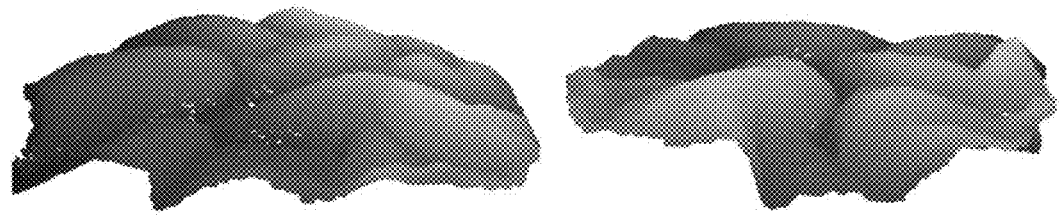
Figure 6A:
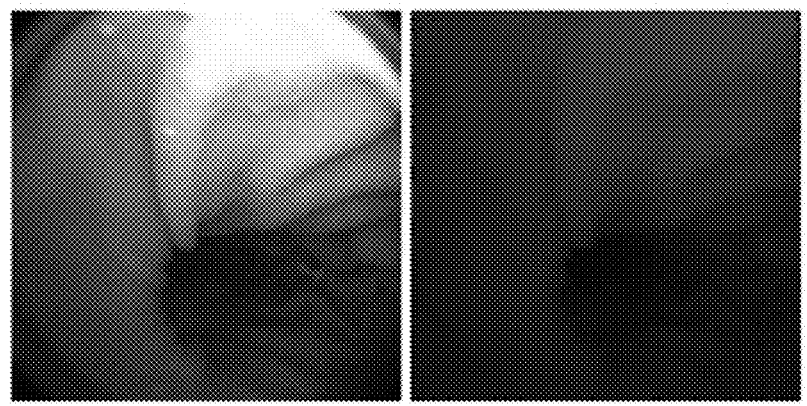
Figure 6B:
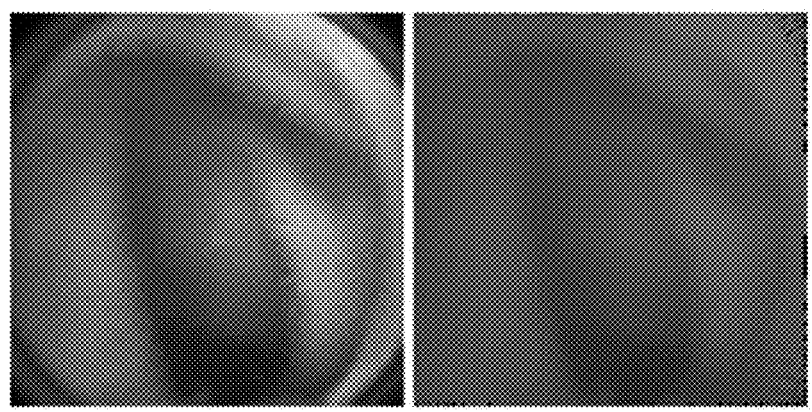
Figure 6C:
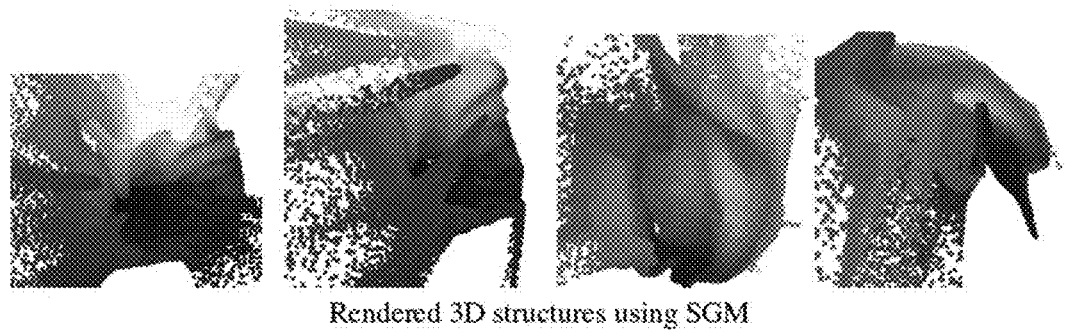
Figure 6D:
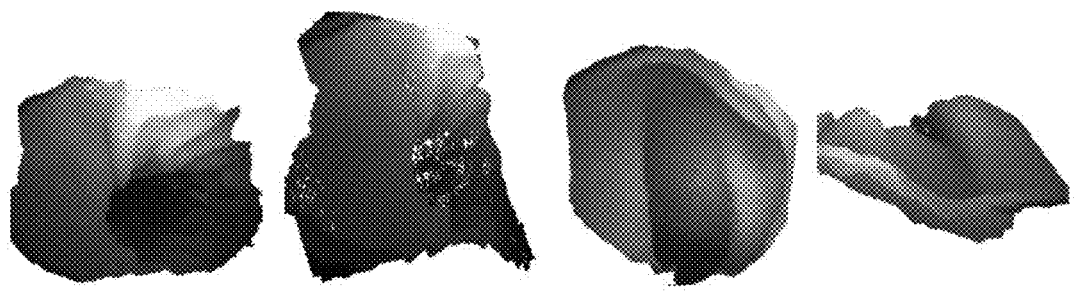
Figure 7A:
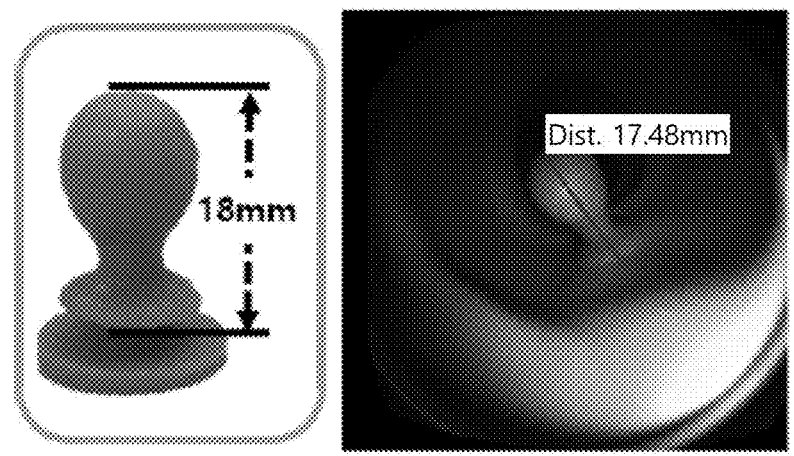
Figure 7B:
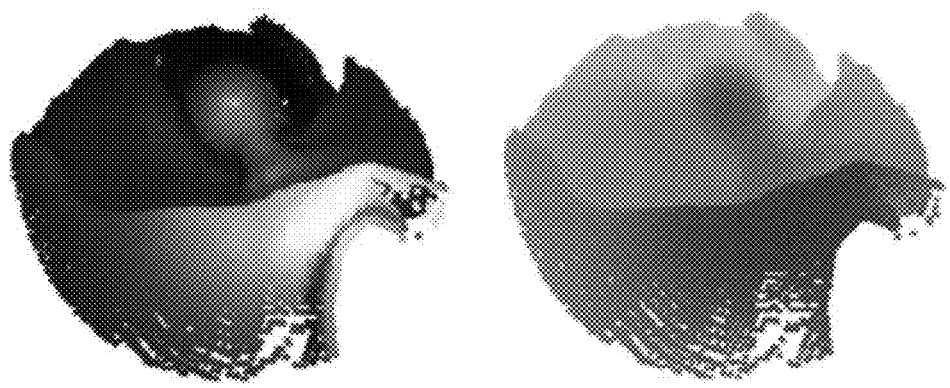
Figure 7C:
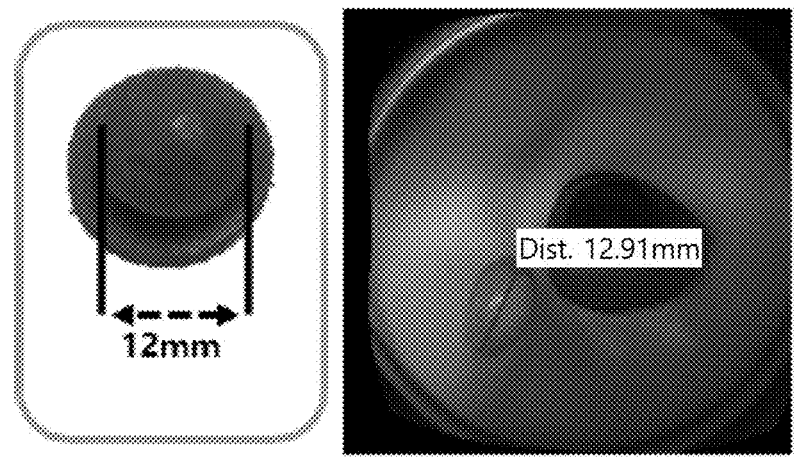
Figure 7D:
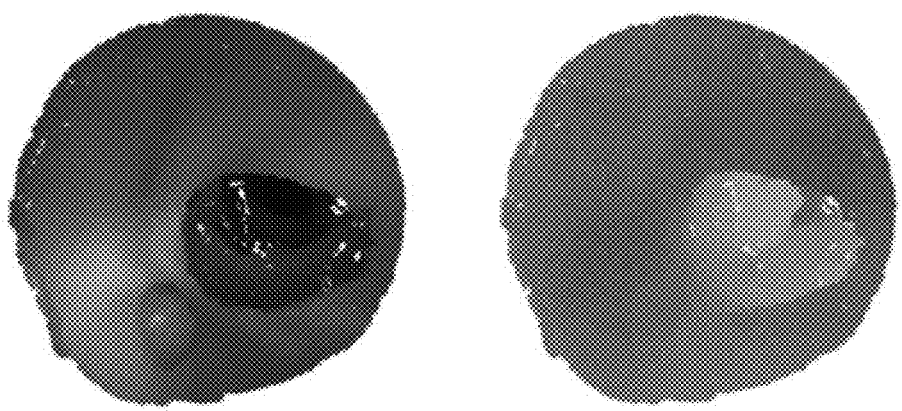

FIGS. 5A to 5C, 6A to 6D, and 7A to 7D illustrate results of endoscopic stereo matching according to embodiments of the present disclosure. Specifically, FIGS. 5A to 5C illustrates experimental results in the small bowel, FIGS. 6 A to 6D illustrates experimental results in the stomach, and FIGS. 7A to 7D illustrates experimental results in a large bowel Phantom model.

As shown in the drawings, a dense depth image can be generated by the endoscopic stereo matching method according to embodiments of the present disclosure, and the 3D structure of the digestive system can be accurately recovered.

6. Endoscopy System

Figure 8:
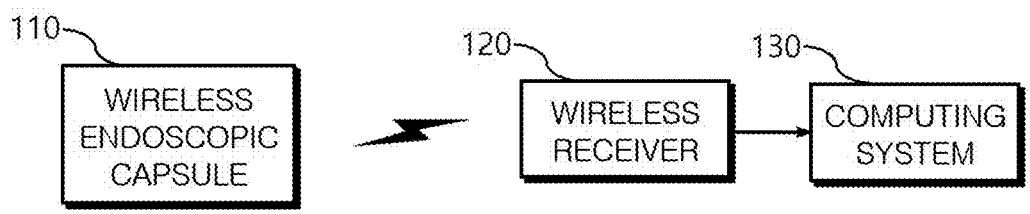
FIG. 8 is a block diagram illustrating an endoscopy system according to another embodiment of the present disclosure.

FIG. 8 is a block diagram of an endoscopy system according to another embodiment of the present disclosure. As shown in FIG. 8, the endoscopy system according to an embodiment of the present disclosure is established by including a wireless endoscopic capsule 110, a wireless receiver 120, and a computing system 130.

The wireless endoscopic capsule 110 includes two cameras, four LED lights, a wireless transmitter, and a battery, and generates a stereo image while moving through the GI tract from the stomach to the large bowel.

The wireless receiver 120 receives the stereo image generated by the wireless endoscopic capsule 110.

The computing system 130 generates a depth image regarding the stereo image received through the wireless receiver 120 and performs stereo matching by using the direct attenuation model described above.

7. Variations

Up to now, the endoscopic stereo matching method and apparatus using the direct attenuation model has been described with reference to preferred embodiments.

In the embodiments of the present disclosure, the depth estimation method using the direct attenuation model is suggested by considering that there is no external light source in an endoscopy environment. Since the only light source in the capsule endoscopy environment is a light source attached to an endoscope, light attenuates as the distance from the light source increases. By physically modeling this characteristic, distance information can be estimated.

In addition, since a depth image estimated through the direct attenuation model gives only relative distance information, embodiments of the present disclosure do not directly use the relative distance information and use the same to assist stereo matching using a binocular image.

The technical idea of the present disclosure may be applied to a computer-readable recording medium which records a computer program for performing the functions of the apparatus and the method according to the present embodiments. In addition, the technical idea according to various embodiments of the present disclosure may be implemented in the form of a computer readable code recorded on the computer-readable recording medium. The computer-readable recording medium may be any data storage device that can be read by a computer and can store data. For example, the computer-readable recording medium may be a read only memory (ROM), a random access memory (RAM), a CD-ROM, a magnetic tape, a floppy disk, an optical disk, a hard disk drive, or the like. A computer readable code or program that is stored in the computer readable recording medium may be transmitted via a network connected between computers.

In addition, while preferred embodiments of the present disclosure have been illustrated and described, the present disclosure is not limited to the above-described specific embodiments. Various changes can be made by a person skilled in the art without departing from the scope of the present disclosure claimed in claims, and also, changed embodiments should not be understood as being separate from the technical idea or prospect of the present disclosure.

What is claimed is:

1. A method for generating a depth image, the method comprising:
    generating a stereo image in an environment where there is no external atmospheric light; and
    estimating a depth image from the stereo image based on scene radiance information of the stereo image and an attenuation trend of a light of an illumination used to generate the stereo image,
    wherein the light is different from the external atmospheric light, and
    wherein the scene radiance information of the stereo image indicates information approximated as a mean of all pixel values of the stereo image.

2. The method of claim 1, wherein the external atmospheric light is a natural light of sunlight.

3. The method of claim 1, wherein the estimating the depth image comprises estimating the depth image by using the following equation:

$$d(p) = \frac{ln(J(p)) - ln(I(p))}{\beta(p)}$$

where d(p) is a depth of a pixel p, J(p) is a scene radiance of the pixel p, I(p) is an observed intensity of the pixel p, and β(p) is a light attenuation coefficient.

4. The method of claim 3, wherein the β(p) is a sum of an absorption coefficient and a scattering coefficient of light.

5. The method of claim 1, wherein the generating comprises generating an internal stereo image filled with a homogeneous matter.

6. The method of claim 3, wherein the β(p) is approximated as a constant value.

7. The method of claim 6, wherein the J(p), corresponding to the scene radiance of the pixel p, is approximated as the mean of all pixel values.

8. The method of claim 1, wherein the estimating the depth image comprises estimating the depth image by using the following equation:

$$d_\beta(p) = \beta d(p) = ln(\bar{I}) - ln(I(p))$$

where $d_\beta(p)$ is a depth image up to a scale factor β regarding the pixel p, $\bar{I}$ is a mean of all pixel values, and I(p) is an observed intensity of the pixel p.

9. The method of claim 8, wherein the scale factor β is determined according to the following equations:

$$\beta = d_\beta(p) / d_s(p)$$

$$d_s(p) = \frac{fB}{|p_x^L - p_x^R|}$$

where $p_x^L$ and $p_x^R$ are positions of matched points from left and right images along an x-axis, f is a focal distance of a left camera, and B is a distance between cameras.

10. An image system comprising:
    a stereo camera configured to generate a stereo image in an environment where there is no external atmospheric light; and
    a computing system configured to estimate a depth image based on scene radiance information of the stereo image and an attenuation trend of light of an illumination used to generate the stereo image,
    wherein the scene radiance information of the stereo image indicates information associated with a mean of all pixel values of the stereo image.

11. A method for generating a depth image, the method comprising:
    estimating a depth image from a stereo image based on scene radiance information of the stereo image and an attenuation trend of light of an illumination used to generate the stereo image,
    wherein the stereo image is generated in an environment where there is no external atmospheric light, and the scene radiance information of the stereo image indicates information associated with a mean of all pixel values of the stereo image; and
    outputting the estimated depth image.

12. The image system of claim 10, wherein the external atmospheric light is a natural light of sunlight.

13. The image system of claim 10, wherein, for the estimating the depth image, the computing system is configured to estimate the depth image by using the following equation:

$$d(p) = \frac{\ln(J(p)) - \ln(I(p))}{\beta(p)}$$

where d(p) is a depth of a pixel p, J(p) is a scene radiance of the pixel p, I(p) is an observed intensity of the pixel p, and β(p) is a light attenuation coefficient.

14. The image system of claim 13, wherein the β(p) is a sum of an absorption coefficient and a scattering coefficient of light.

15. The image system of claim 10, wherein, for the generating, the computing system is configured to generate an internal stereo image filled with a homogeneous matter.

16. The image system of claim 13, wherein the β(p) is approximated as a constant value.

17. The image system of claim 16, wherein the J(p), corresponding to the scene radiance of the pixel p, is approximated as the mean of all pixel values.

18. The image system of claim 10, wherein, for the estimating the depth image, the computing system is configured to estimate the depth image by using the following equation:

$$d_\beta(p) = \beta d(p) = ln(\bar{I}) - ln(I(p))$$

where $d_\beta(p)$ is a depth image up to a scale factor $\beta$ regarding the pixel p, $\bar{I}$ is a mean of all pixel values, and I(p) is an observed intensity of the pixel p.

19. The image system of claim 18, wherein the scale factor $\beta$ is determined according to the following equations:

$$\beta = d_\beta(p) / d_s(p)$$

$$d_s(p) = \frac{fB}{|p_x^L - p_x^R|}$$

where $p_x^L$ and $p_x^R$ are positions of matched points from left and right images along an x-axis, f is a focal distance of a left camera, and B is a distance between cameras.

* * * * *